United States Patent
Takahashi et al.

(10) Patent No.: US 6,783,518 B2
(45) Date of Patent: Aug. 31, 2004

(54) FLOAT FOR LIQUID WASTE DISPOSAL APPARATUS

(75) Inventors: Masao Takahashi, Gunma-ken (JP); Kazuo Koike, Tokyo (JP); Eiichi Takano, Tokyo (JP); Nobuo Murata, Tokyo (JP); Masashi Suzuki, Nagano-ken (JP)

(73) Assignees: Gunma Koike Co., Ltd., Gunma-ken (JP); Koike Medical Co., Ltd., Tokyo (JP)

( * ) Notice: Subject to any disclaimer, the term of this patent is extended or adjusted under 35 U.S.C. 154(b) by 387 days.

(21) Appl. No.: 09/888,453

(22) Filed: Jun. 27, 2001

(65) Prior Publication Data

US 2003/0004475 A1 Jan. 2, 2003

(51) Int. Cl.[7] .............................. A61M 1/00; F16K 31/18
(52) U.S. Cl. .......................................... 604/319; 137/430
(58) Field of Search ................................ 604/317–322, 604/326; 137/430, 433

(56) References Cited

U.S. PATENT DOCUMENTS

| | | | | |
|---|---|---|---|---|
| 5,185,007 A | * | 2/1993 | Middaugh et al. | .......... 604/320 |
| 5,234,419 A | * | 8/1993 | Bryant et al. | ................ 604/320 |
| 5,238,582 A | * | 8/1993 | Hori et al. | ................... 210/749 |
| 5,279,602 A | * | 1/1994 | Middaugh et al. | .......... 604/320 |
| 5,284,621 A | * | 2/1994 | Kaufman | ...................... 422/32 |
| 5,307,819 A | * | 5/1994 | Trautmann et al. | ......... 600/580 |
| 5,401,261 A | * | 3/1995 | Gunya et al. | ................. 604/319 |
| 5,507,078 A | * | 4/1996 | Gunya et al. | ................. 27/21.1 |
| 6,615,862 B2 | * | 9/2003 | Takahashi et al. | .......... 137/433 |
| 2002/0026160 A1 | * | 2/2002 | Takahashi et al. | .......... 604/319 |

* cited by examiner

Primary Examiner—John J. Calvert
Assistant Examiner—Michael G. Bogart
(74) Attorney, Agent, or Firm—Townsend & Banta

(57) ABSTRACT

The object of this invention of a float for liquid waste disposal apparatus enables the content inside a container to be easily visually recognizable and allows a faster and steadier solidification of an absorbed liquid waste.

The connection plates 5c connects the annular member 5a serving as the guide member to the outer peripheral portion of the cup portion 5b retaining the water-absorptive material 6 wherein the annular member 5a is restrained by the inner wall 26 of the lying member L for preventing the float 5 from revolving in the vertical direction. The liquid waste 21 absorbed from the upper portion and into the lying member L flows downward via the flow path structured with the interstitial portion 27 formed between the annular member 5a and the cup portion 5b and the interstitial portion 28 formed between the inner wall 26 of the lying member L and the annular member 5a.

16 Claims, 13 Drawing Sheets

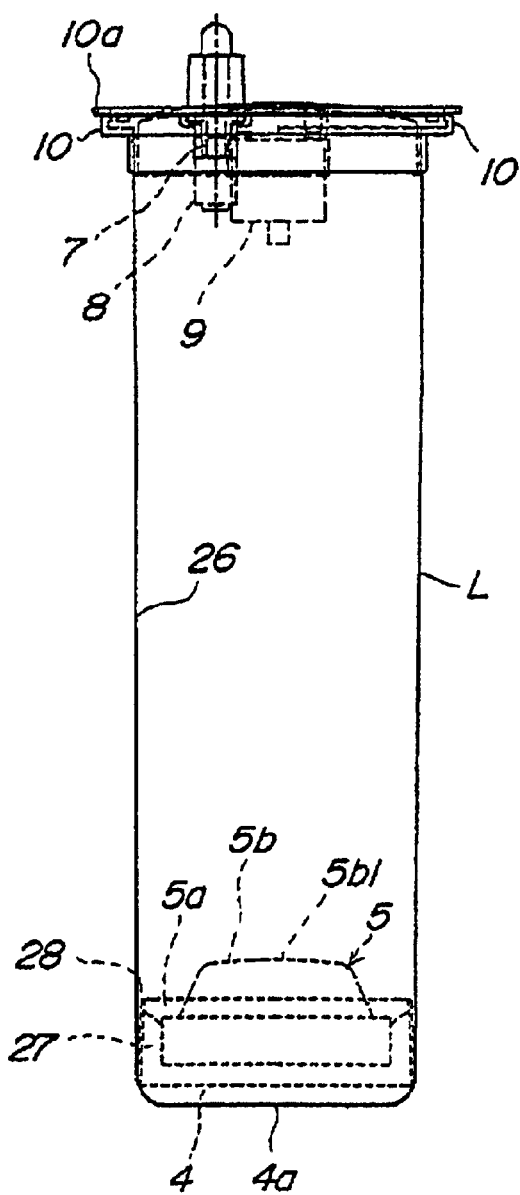
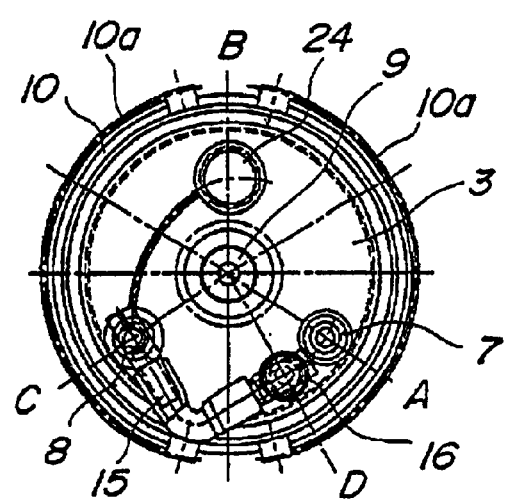
FIG.5(a)
FIG.5(b)

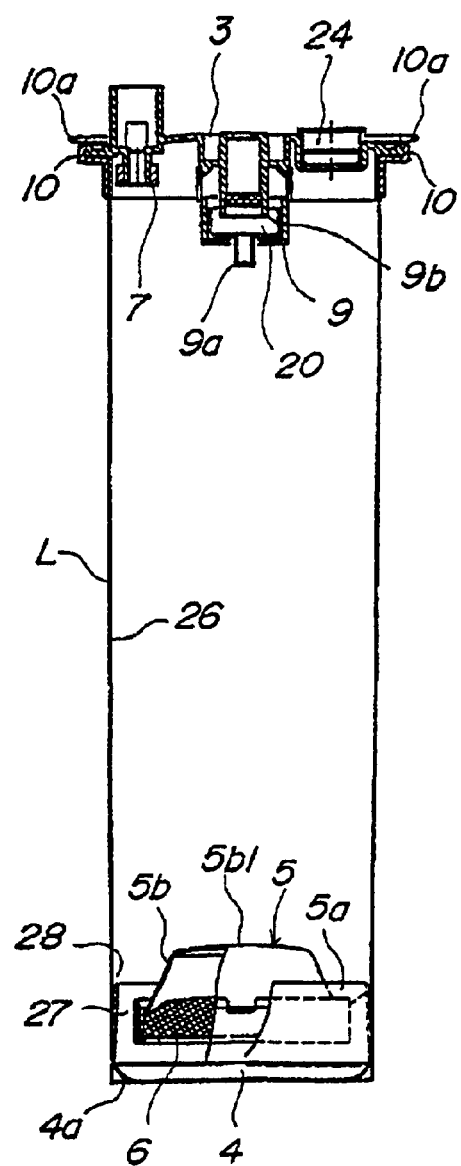
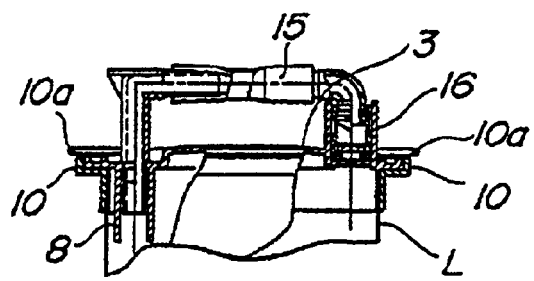
FIG.6(a)
FIG.6(b)

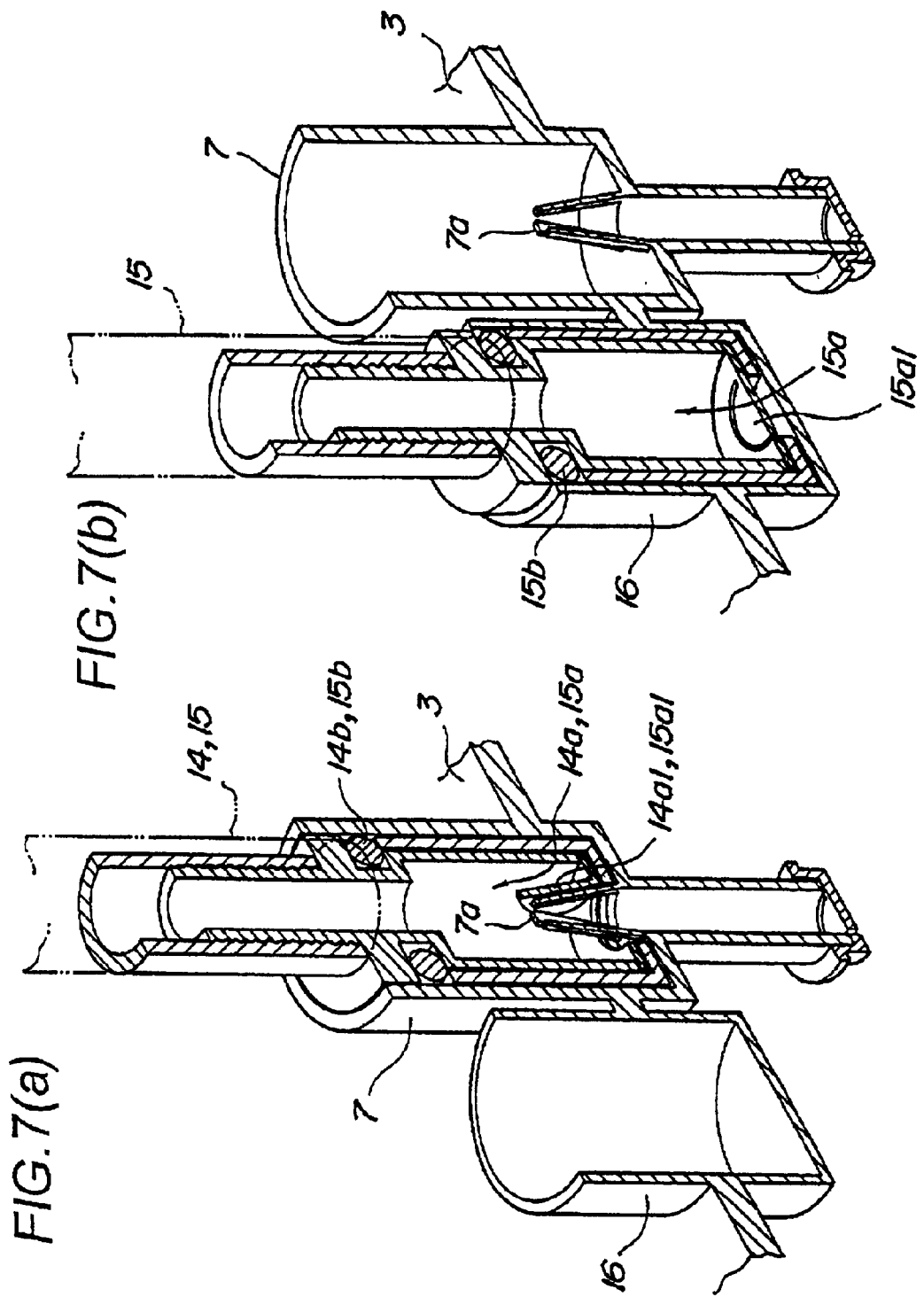

FLOAT FOR LIQUID WASTE DISPOSAL APPARATUS

BACKGROUND OF THE INVENTION

1. Field of the Invention

This invention relates to a float used for a liquid waste disposal apparatus serving to absorb, to solidify and to dispose a liquid waste such as unwanted blood, other body fluids, secretion derived from a medical scene or pus or physiological sodium chloride solution used for cleansing affected areas.

2. Description of Related Art

A liquid waste (e.g. unwanted blood, other body fluids, secretion, pus, or physiological sodium chloride solution used for cleansing affected areas) derived from medical scenes, particularly at a scene of surgical operation, is collected into a container or a collecting bag for disposal and incineration by an absorbing apparatus.

However, since the liquid waste may contain a harmful bacteria or the like, a secondary infection may occur among medical employees, hospital patients and the like, when the container or the collecting bag becomes damaged or when an excessive amount of the liquid waste is absorbed exceeding a capacity of the collecting bag.

For preventing thus created problem, an apparatus for solidifying a liquid waste with a water-absorptive material arranged inside a collecting bag is provided and methods for arranging the liquid waste solidifying water-absorptive material inside the collecting bag are provided such as: a method of forming a collecting bag with a non-water permeable sheet and a water-absorptive sheet stuck with each other in which the water-absorptive sheet is arranged as an inner surface, a method of dropping a prepared water-absorptive material into a collecting bag after an absorption of liquid waste, or a method of fixing a water-absorptive material at a bottom portion of a collecting bag.

Nevertheless, the foregoing conventional example of forming a collecting bag with a non-water permeable sheet and a water-absorptive sheet stuck with each other caused an inner portion to be unable to be seen from outside and also caused difficulty of folding and also caused inconvenience during storage and transport owing to a multiple structure of the collecting bag.

With the foregoing conventional example of dropping a prepared water-absorptive material into a collecting bag after absorption of liquid waste, further absorption could not be performed once solidification is completed and there remained a danger when toppled during the middle of a process since solidification would not proceed until the water-absorptive material is dropped inside the collecting bag.

With the foregoing conventional example of fixing a water-absorptive material at a bottom portion of a collecting bag, a solidifying speed would decrease in association with the proceeding of the liquid waste absorption process.

It is an object of this invention to solve the aforementioned problems by providing a float for a liquid waste disposal apparatus capable of making the amount of the content inside a container more visible and capable of making solidification of an absorbed liquid waste faster and steadier.

SUMMARY OF THE INVENTION

This invention for solving the foregoing problems relates to a float for a liquid waste disposal apparatus contained in a floatable state inside a container for containing an absorbed liquid waste comprising: a solidifying agent retaining portion for retaining a solidifying agent; a revolution prevention member restrained by an inner wall of the container to prevent revolution in a vertical direction; and a flow path for flowing downward a liquid waste absorbed from an upper portion into the container.

Thus structured, the flow path flows downward a liquid waste absorbed from an upper portion into the container. The revolution prevention member arranged to the float and restrained by an inner wall of the container serves to prevent the float from revolving in a vertical direction and thus enables the float to steadily float inside the container. The solidifying agent retained by the solidifying agent retaining portion serves to solidify the liquid waste.

A solidifying agent could be provided within the container since the float itself is capable of retaining a solidifying agent; subsequently, the solidification of liquid waste inside the container enables the container to be disposed one by one and thus enables sanitary disposal.

Structuring the revolution prevention member by forming a guide member at a sidewall of a float body or at an outer peripheral portion of the float body enables a desirable simple structure.

Structuring the flow path by forming an interstitial portion arranged between the sidewall of the float body and the inner wall of the container and/or an interstitial portion arranged between the float body and the guide member arranged at the outer peripheral portion of the float body enables a desirable simple structure.

Another structure of the float for a liquid waste disposal apparatus regarding this invention relates to a float for a liquid waste disposal apparatus contained in a floatable state inside a container for containing an absorbed liquid waste comprising: an annular solidifying agent retaining portion for retaining a solidifying agent, wherein a hollow portion of the annular solidifying agent retaining portion forms a flow path for flowing downward a liquid waste absorbed from an upper portion into the container and thus, a sidewall of the annular solidifying agent retaining portion is restrained by an inner wall of the container to prevent revolution in a vertical direction.

Thus structured, a flow path formed of a hollow portion of the annular solidifying agent retaining portion enables a liquid waste absorbed into the container to flow downward from an upper portion. The annular revolution prevention member restrained by an inner wall of the container serves to prevent the float from revolving in a vertical direction and thus enables the float to steadily float inside the container. The solidifying agent retained by the annular solidifying agent retaining portion serves to solidify the liquid waste.

A solidifying agent could be provided inside the container since the float itself is capable of retaining a solidifying agent; subsequently, the solidification of liquid waste inside the container enables the container to be solely and sanitarily disposed.

Another structure of the float for a liquid waste disposal apparatus regarding this invention relates to a float for a liquid waste disposal apparatus contained in a floatable state inside a container for containing an absorbed liquid waste comprising: an annular solidifying agent retaining portion for retaining a solidifying agent; and a revolution prevention member having a stick-like, or pipe-like, or wire-like structure and being inserted through the hollow portion of the annular solidifying agent retaining portion, wherein the hollow portion of the annular solidifying agent retaining portion forms a flow path for flowing downward a liquid waste absorbed from an upper portion into the container.

According to thus structure, the liquid waste absorbed from an upper portion flows downward into the container via the hollow portion of the annular solidifying agent retaining portion serving as the flow path. A revolution prevention member having a stick-like, or pipe-like, or wire-like structure and being inserted through the hollow portion of the annular solidifying agent retaining portion is restrained by an inner wall of the container so as to prevent the float from revolving in a vertical direction and thus enabling the float to steadily float inside the container. The solidifying agent retained by the annular solidifying agent retaining portion serves to solidify the liquid waste. A solidifying agent could be provided within the container since the float itself is capable of retaining a solidifying agent; subsequently, the solidification of liquid waste inside the container enables the container to be solely and sanitarily disposed.

An activation of an absorption stop valve causes absorption to automatically stop when the float inside the container reaches an upper end portion of the container by arranging the absorption stop valve at an inner side of the upper portion of the container in which the absorption stop valve is activated when pushed upward by an upward-pushing portion; subsequently, the upward-pushing portion of the float activates the absorption stop valve so as to automatically stop the absorption of liquid waste before the container becomes full and also serves to prevent an air pump or the like from malfunctioning from an excessive absorption into the container.

By forming a downward opening portion and by stretching and spreading a water permeable sheet (e.g. traditional Japanese paper) in a state where a liquid waste absorbed into the container flows downward from the upper portion via the flow path, the liquid waste could permeate into the water permeable sheet and contacts to a solidifying agent and then, the solidifying agent could swell to tear the water permeable sheet and then, the solidifying agent is mixed into the liquid waste from a downward opening portion of the solidifying agent retaining portion so as to solidify the liquid waste below the float.

By forming a downward opening portion and by stretching and spreading a water-soluble film in a state where a liquid waste absorbed into the container flows downward from the upper portion via the flow path, the liquid waste contacts to the water-soluble sheet and dissolves the water-soluble sheet and then, the solidifyng agent is mixed into the liquid waste from a downward opening portion of the solidifying agent retaining portion so as to solidify the liquid waste below the float.

By controlling a specific gravity of the float for a liquid waste disposal apparatus to become less than 1, a liquid surface could be easily confirmed from outside by checking the position of the float since the float would always remain afloat at a gas-liquid interface; accordingly, an amount of the absorbed liquid waste could easily be visually recognized and could also function as a level gauge.

By having at least one portion of the float for a liquid waste disposal apparatus in a florescent color or in a color distinguishable between a color of a liquid waste, a liquid surface could easily be confirmed from outside since the position of the float could easily be visually recognized; accordingly, an operator could positively confirm the used capacity as well as the remaining capacity of the container.

BRIEF DESCRIPTION OF THE DRAWINGS

The above and other objects and features of the invention are apparent to those skilled in the art from the following preferred embodiments thereof when considered in conjunction with the accompanied drawings, in which:

FIG. 5($a$) is an outer front view showing a structure of a float for a liquid waste disposal apparatus regarding this invention and a container containing the float; FIG. 5 ($b$) is an outer plane view showing a structure of a container containing a float for a liquid waste disposal apparatus regarding this invention;

FIG. 6($a$) is a cross-sectional view showing B subtracted by A of FIG. 5($b$); FIG. 6($b$) is a cross-sectional view showing D subtracted by C of FIG. 5($b$);

FIG. 7 is an explanatory view showing a function of a valve member when a connection tube or a patient hose is connected to a closing stopper and an absorption port arranged at a lid of a ceiling portion of a container;

DESCRIPTION OF THE PREFERRED EMBODIMENTS

Figure 1:
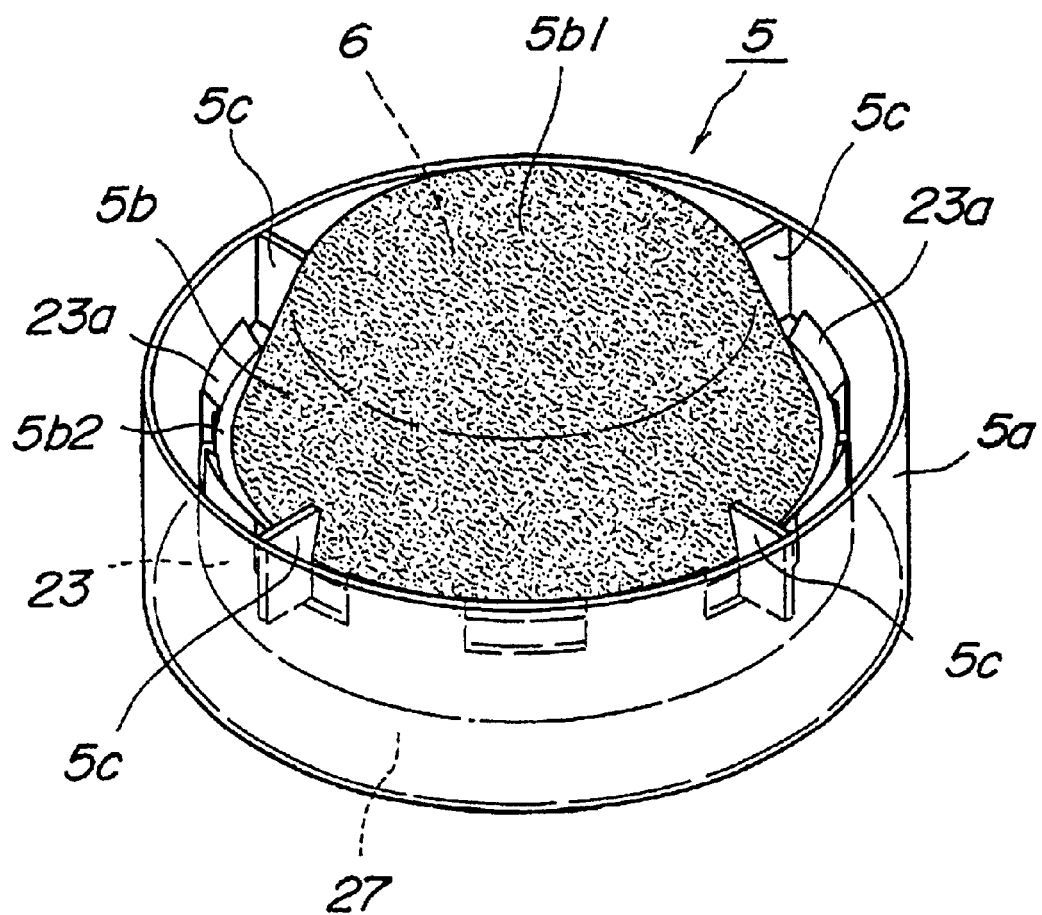
FIG. 1 is a perspective explanatory view showing a structure of a first embodiment of a float for a liquid waste disposal apparatus regarding this invention.
Figure 2:
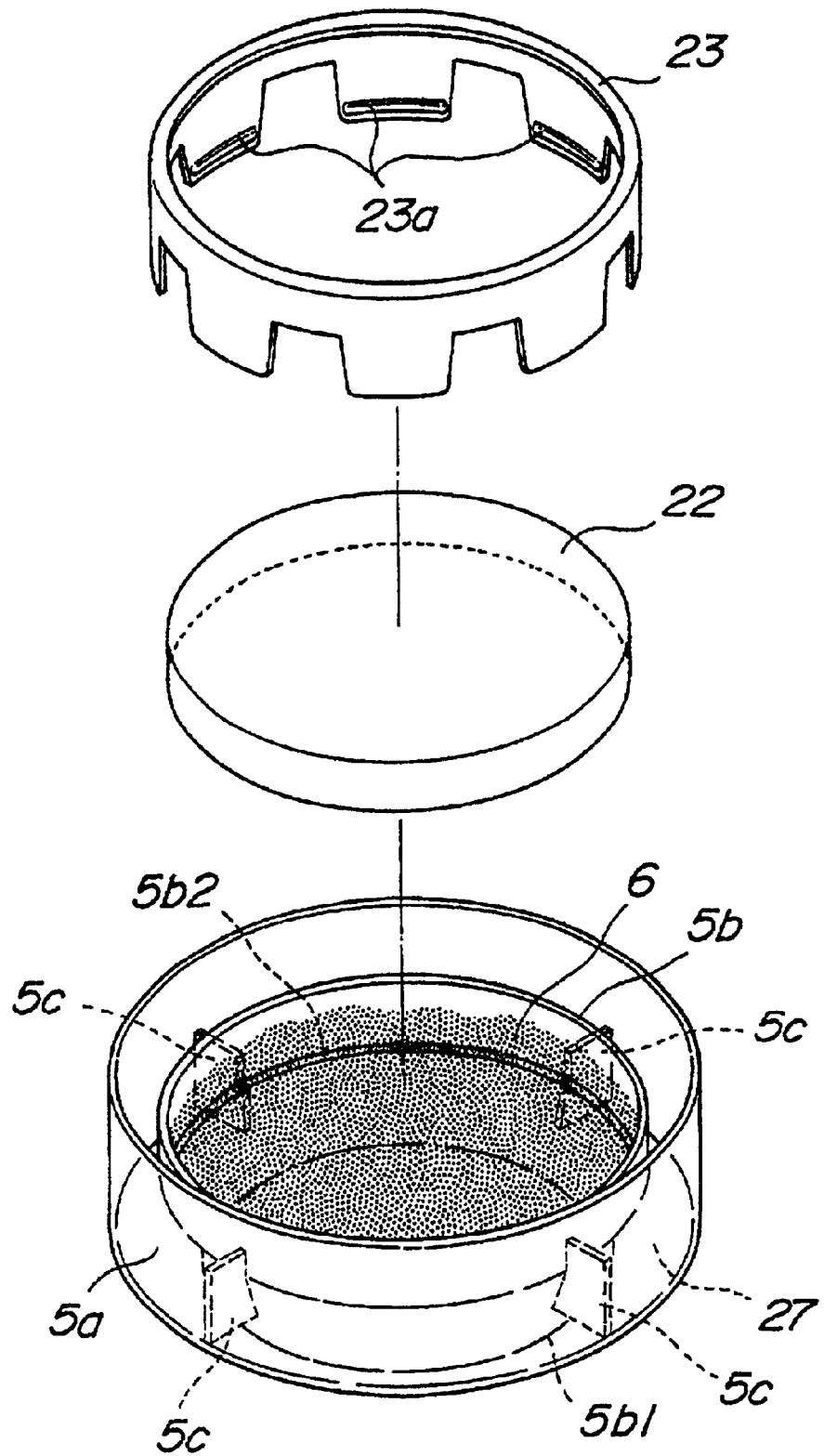
FIG. 2 is an exploded perspective view showing the first embodiment of a float for a liquid waste disposal apparatus.

An embodiment of the float for a liquid waste disposal apparatus regarding this invention will hereinafter be described with reference to the drawings. FIG. 1 is a perspective explanatory view showing a structure of a first embodiment of a float for a liquid waste disposal apparatus regarding this invention; and FIG. 2 is an exploded perspective view showing the first embodiment of a float for a liquid waste disposal apparatus.

Figure 3:
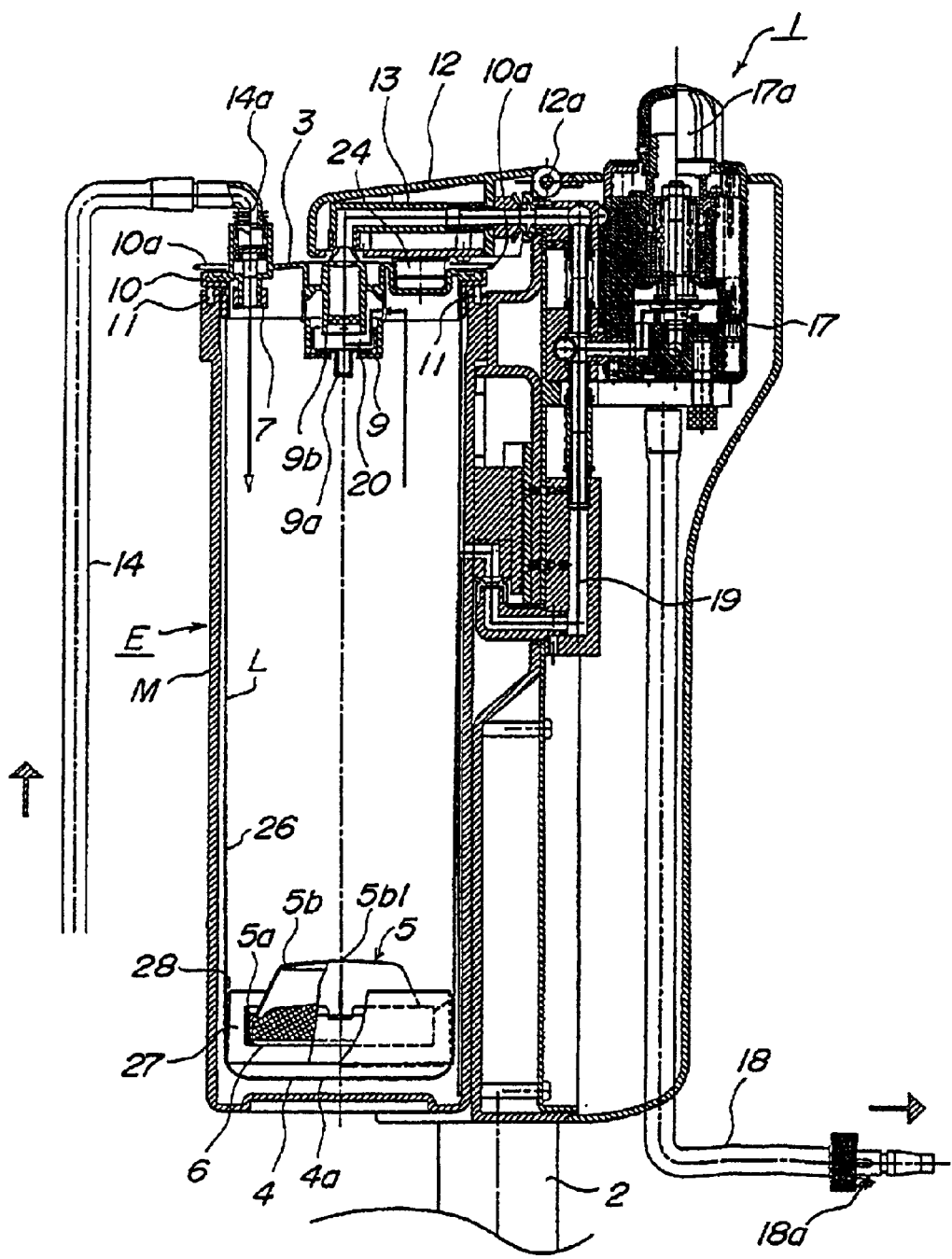
FIG. 3 is a vertical cross-sectional explanatory view showing a structure of a liquid waste disposal apparatus built with a float for a liquid waste disposal apparatus regarding this invention.
Figure 4:
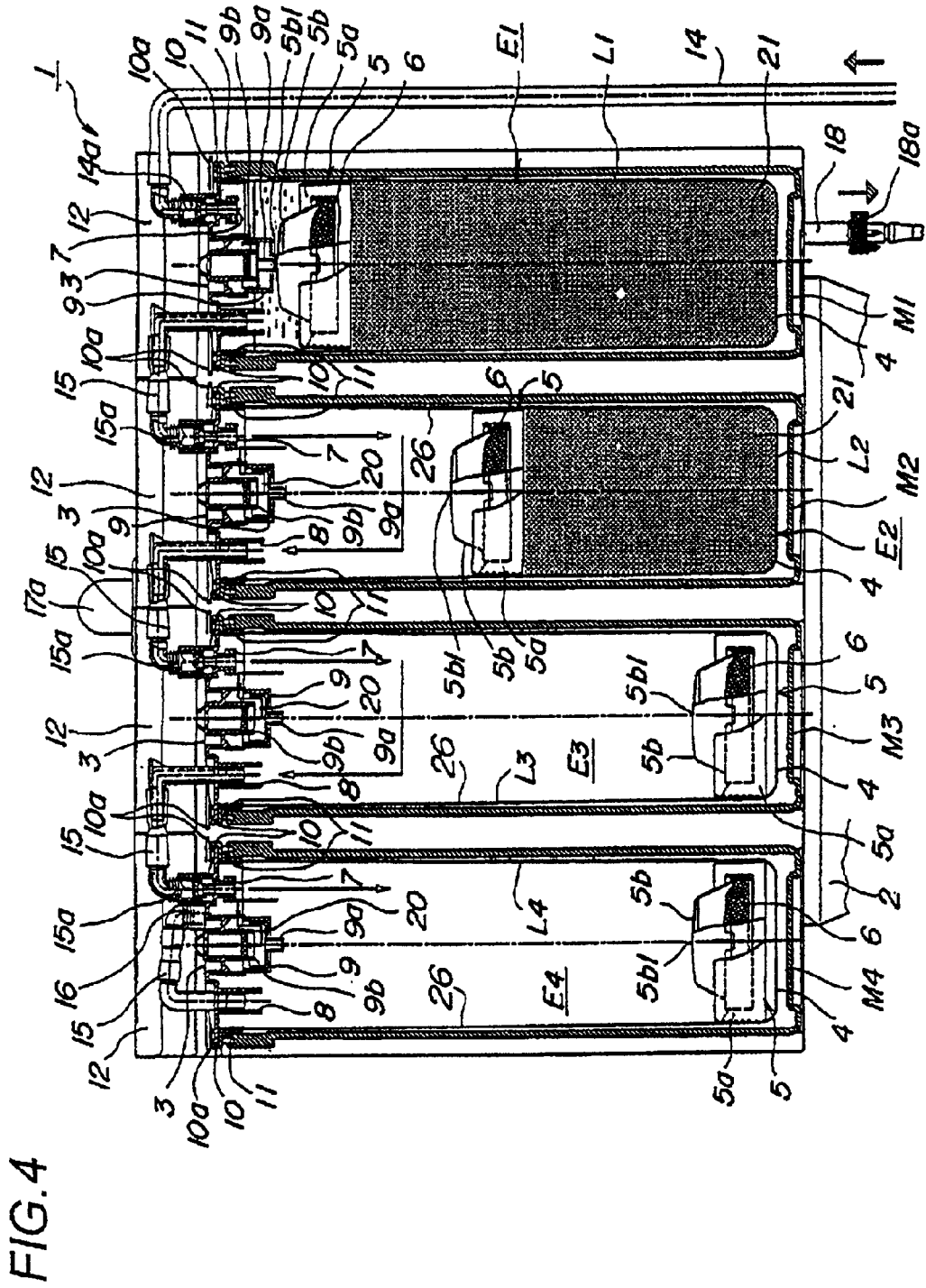
FIG. 4 is a side cross-sectional explanatory view showing a structure of a liquid waste disposal apparatus built with a float for a liquid waste disposal apparatus regarding this invention.

FIG. 3 is a vertical cross-sectional explanatory view showing a structure of a liquid waste disposal apparatus built with a float for a liquid waste disposal apparatus regarding this invention; and FIG. 4 is a side cross-sectional explanatory view showing a structure of a liquid waste disposal apparatus built with a float for a liquid waste disposal apparatus regarding this invention.

FIG. 5(a) is an outer front view showing a structure of a float for a liquid waste disposal apparatus regarding this invention and a container containing the float; FIG. 5 (b) is an outer plane view showing a structure of a container containing a float for a liquid waste disposal apparatus regarding this invention; FIG. 6(a) is a cross-sectional view showing B subtracted by A of FIG. 5(b); and FIG. 6(b) is a cross-sectional view showing D subtracted by C of FIG. 5(b).

FIG. 7 is an explanatory view showing a function of a valve member when a connection pipe or a patient hose is connected to a closing stopper and an absorption port arranged at a lid of a ceiling portion of a container.

The embodiment described hereinafter relates to a float for a liquid waste disposal apparatus suitably used for a medical liquid waste disposal apparatus in which a liquid waste 21 (such as dispensable blood, other body fluids, secretion, pus, or physiological sodium chloride solution used for cleansing affected areas produced during operation and treatment) is absorbed and contained inside a lying member L serving as a container contained inside a canister bottle E; wherein the float staying afloat on top of the liquid waste 21 inside the lying member L while mixing a water-absorptive material 6 into the liquid waste 21 so as to solidify the liquid waste 21 for enabling incineration of the lying member L.

As shown in FIG. 1 and FIG. 2, a float for a liquid waste disposal apparatus 5 regarding this invention comprises: a cup portion 5b serving as a solidifying agent retaining portion for retaining a solidifying agent, that is, a water-absorptive material 6 in which the solidifying agent retaining portion forms a float body; and an annular member 5a serving as a guide member arranged at a peripheral portion of the cup portion 5b in which the annular member 5a is restrained by an inner wall 26 of a container shown in FIG. 3 through FIG. 6 (that is, a flexible lying member L) to serve as a revolution prevention member for preventing the float 5 from revolving in an up-down direction (overturning in an up-down direction), wherein the cup portion 5b and the annular member 5a are connected by a plurality of connecting plates 5c.

The float 5 is supported by an inner edge portion of the annular member 5a serving as a guide member in a manner where a solidifying agent such as a water-absorptive polymer is filled and retained by the cup portion 5b serving as a solidifying agent retaining portion in which the cup portion 5b has a face down shape with a downward opening; and thus, the annular member 5a, the cup portion 5b and the connecting plate 5c according to this embodiment is formed to have a specific gravity less than 1.

An outer diameter of the annular member 5a of the float 5 is formed smaller than an inner diameter of the lying member L, a bottom portion of the cup 5b is opened in a state where the float 5 is contained inside the lying member L.

In a filling process of the water-absorptive material 6 into the cup portion 5b of the float 5, as shown in FIG. 2, after the water-absorptive material 6 has been filled into the cup portion 5b where the float 5 is in an upside down state, a fixing ring 23 is engaged to peripheral rim of a opening portion of the cup portion 5b having a water permeable sheet 22 e.g. Japanese traditional paper or a water-soluble film in a spread and stretched state and further, a claw portion 23a of the fixing ring 23 is engaged to step portion 5b2 formed at a peripheral edge portion of the cup portion 5b.

An interstitial portion 27 is formed between the cup portion 5b and the annular member 5a. An inner diameter of the lying member L is predetermined to have a prescribed length larger than the outer diameter of the annular member 5a of the float 5, and an interstitial portion 28 is also arranged between the annular member 5a and the lying member L. The interstitial portions 27, 28 serves to form a flow path so that the liquid waste 21 absorbed from above and into the lying member L would flow downward under the float 5.

The lying member L containing the float 5 and the absorbed liquid waste 21 has a lid 3 fixed to a ceiling portion; and as shown in FIG. 3 and FIG. 4, thus lying member L is in a detachably contained inside a bottle M serving as an outer container.

As shown in FIG. 4, regarding a liquid waste disposal apparatus 1 of this embodiment, four canister bottles E are connected in series and arranged in a straight line and are supported by a stand 2.

The bottle M serving as an outer container is supported by the stand 2 in a detachable attached manner, and a caster (not shown) is attached to a leg portion of the stand 2. Thus structure allows the stand 2 to steadily move the four canister bottles E in a state where the four canister bottles E are supported and arranged in a straight line.

The bottle M is a transparent plastic cylindrical container having an engagement portion arranged at a rear side for detachably engaging with the stand 2 and a graduation formed at a surface for indicating capacity.

As shown in FIG. 5 and FIG. 6, the lying member L is a united body having a circular plastic lid 3 thermally welded to an opening rim portion of a flexible cylindrical transparent bag 4 form from a low density polyethylene; a plastic ring-shaped holder 10 is engaged and fixed to a peripheral portion of the lid 3.

A path portion of the holder 10 is engaged and fixed to an opening rim portion of the bottle M and a catch 10a is molded to the holder 10 forming a united body.

The canister bottle E containing the lying member L inside the bottle M allows the liquid waste 21 absorbed and contained inside the lying member L to be easily visually recognizable; further, the amount of the liquid waste 21 and a remaining capacity could be confirmed by the graduation formed at the surface of the bottle M.

The float 5 capable of floating is arranged above an inside bottom portion 4a of the lying member in which the float has a specific gravity less than 1 and retains a water-absorptive material 6 e.g. water-absorptive polymer serving as a solidifying agent inside the cup portion 5b.

As shown in FIG. 4, an absorption port 7 and an discharge port 8 arranged at the lid 3 are liquid-communication to an inside of the lying member L wherein the absorption port 7 absorbs the liquid waste 21 into the lying member L and the discharge port 8 discharges the liquid waste 21 to the absorption port 7 of an adjoining lying member 21.

An exhaust port 9 exhausting air from the lying member 21 for creating a negative pressured state is arranged at a central portion of the lid 3 in an air-communication manner to the inside of the lying member L.

When inserting the lying member L into the bottle M, as shown in FIG. 3 and FIG. 4, a canister head 12 arranged opposite to the stand 2 and pivotally movable around a pivotal movement shaft 12a as a center would pivotally move and open so that the lying members L1, L2, L3, L4 could respectively be inserted into the four bottles M1, M2, M3, M4 fixed to the stand 2 and arranged in a straight line.

As shown in FIG. 3 and FIG. 4, when the lying member L is inserted into the bottle M, a cylindrical portion of the holder engaged to an outer peripheral portion of the lid 3 arranged at the ceiling portion of the lying member L is engagedly inserted to the opening rim portion of the bottle M and thus, a packing 11 arranged at an opening peripheral rim of the bottle M contacts to a collar portion of the holder 10.

When the canister head 12 is closed by pivotally moving the canister head downward around the pivotal movement shaft 2a as the center, as shown in FIG. 3, an absorption path 13 arranged at the canister head 12 is connected in air-communication with the exhaust port 9 arranged at the lid 3 of the lying member L, and at the same time, the lid 3 of the lying member L is fixed to the bottle M via the holder 10 creating an air-tight sealed state at the space between the bottle M and the lying member L via the packing 11 where the lid 3 and the holder 10 are unitedly pressed against the bottle M fixed by the stand 2.

As shown in FIG. 4, a patient hose 14 is connected to the absorption port 7 arranged at the lid 3 of a primary lying member L1 in a state where a primary canister bottle E1, a secondary canister bottle E2, a third canister bottle E3 and a fourth canister bottle E4 are disposed in a straight line and arranged in an order starting from the primary lying member L1 to the secondary canister bottle E2 to the third canister bottle E3 and to the fourth canister bottle E4; the patient hose 14 is applied to a portion such as an affected portion of a patient so as to absorb the liquid waste 21 such as dispensable blood, other body fluids, secretion, pus, or physiological sodium chloride solution used for cleansing affected areas produced during operation and treatment.

The absorption port 7 arranged at the lid 3 of the secondary lying member L2 is connected to the discharge port 8 arranged at the lid 3 of the primary lying member L1 via a connection pipe 15, and the absorption port 7 arranged at the lid 3 of the third lying member L3 is connected to the discharge port 8 arranged at the lid 3 of the secondary lying member L2 via the connection pipe 15, and the absorption port 7 arranged at the lid 3 of the fourth lying member L4 is connected to the discharge port 8 arranged at the lid 3 of the third lying member L3 via the connection pipe 15.

A closing stopper 16 arranged at the lid 3 of the fourth lying member L4 is connected to the discharge port 8 arranged at the lid 3 of the lying member L4 of the lastly disposed step, that is, the canister bottle E4 via the connection pipe 15; accordingly, the discharge port 8 arranged at the lid 3 of the lying member L4 of the lastly disposed step, that is, the canister bottle E4 becomes closed.

As shown in FIG. 4, an end portion of the connection pipe 15 is connected to the discharge port 8 arranged at the lid 3 of the respective lying member L in a pivotally movable and airtight manner. The pivotally moving the connection pipe 15 around the discharge port 8 as a center allows another end portion of the connection pipe 15 to selectively connect with either the absorption port 7 formed at the lid 3 of a lying member L adjoined downstream (left side of FIG. 4) or the closing stopper 16 of thus lid 3.

A valve member 15a is arranged at an opening rim portion of the connection pipe 15 and as shown in FIG. 7(a), when connecting the opening rim portion of the connection pipe 15 to the absorption port 7, the connection pipe 15 is in air-communication with the absorption port 7 in which a projecting portion 7a arranged at a surrounding of an opening portion of the absorption port 7 is pushed upward to open a rubber valve 15a1 formed at the valve member 15a and further, a letter O shaped ring arranged at an outer peripheral portion of the valve member 15a is pressingly contacting to an inner wall of an opening portion of the absorption port 7 so as to maintain an airtight state.

As shown in FIG. 7(b), when connecting the opening rim portion of the connection pipe 15 to the closing stopper 16, the connection pipe 15 is closed in a state where a letter O shaped ring arranged at an outer peripheral portion of the valve member 15a is pressingly contacting to an inner wall of an opening portion of the closing stopper 16 so as to maintain an airtight state while the rubber valve 15a1 remains shut.

Likewise, a valve member 14a is arranged at an end portion connected to the patient hose 14 on the side of the liquid waste disposal apparatus 1, and in a state where the end portion of the patient hose 14 is connected to the absorption port 7, the patient hose 14 is in air-communication with the absorption port 7 in which a projecting portion 7a arranged at a surrounding of an opening portion of the absorption port 7 is pushed upward to open a rubber valve 14a1 formed at the valve member 14a and further, a letter O shaped ring arranged at an outer peripheral portion of the valve member 14a is pressingly contacting to an inner wall of an opening portion of the absorption port 7 so as to maintain an airtight state.

As shown in FIG. 3, a controller 17 having an adjustment handle 17a for adjusting an absorption pressure (vacuum pressure) is arranged to the stand 2; the controller 17 is connected to a primary absorption hose 18 connected to a terminal takeout port (outlet valve) or an air pump of an absorption piping of a medical gas piping installation in which an adjusted absorbing pressure of the controller 17 causes an inside of the lying member L to become negative pressure via the absorption path 13 and an absorption path 20 of the exhaust port 9.

On the other hand, as shown in FIG. 3, the absorption path 13 is in air-communication with an absorption path 19 in which the absorption path 19 is connected to a gap between the bottle M and the lying member L. Since both an absorption pressure inside the lying member L and an absorption pressure of the gap between the bottle M and the lying member L are negatively pressured with an equal absorption pressure, the air pressure inside and outside of the lying member L arranged inside the bottle M becomes equal and thus, a steady absorption could be performed while maintaining a state shown in FIG. 3 without causing the lying member L formed with a flexible sheet to expand and contract.

An absorption stop valve 9a is arranged at the exhaust port 9 and thus at an inner side of an upper portion of the lying member L; further, as shown by the canister bottles E2, E3, E4 of FIG. 4, a self-weight of the absorption stop valve 9a allows the absorption stop valve 9a to maintain a downward position until the float 5 floats to reach the ceiling portion and subsequently, the absorption path 20 in air-communication with the absorption path 13 from inside the lying member L could be maintained.

On the other hand, as shown by the canister bottle E1 of FIG. 4, when the liquid waste 21 is absorbed into the lying member L to elevate the float 5 until the float 5 reaches the ceiling portion of the lying member L, a ceiling edge surface 5b1 of the float 5 serving as an upward-pushing portion for activating the absorption stop valve 9a by pushing the absorption stop valve 9a upward makes contact to the absorption stop valve 9a and pushes the absorption stop valve 9a upward against the self-weight of the absorption stop valve 9a and causes the absorption path 20 in air-communication with the absorption path 13 from inside the lying member L to become closed.

Once the absorption stop valve 9a is pushed upward to close the absorption path 20, owing to an absorbing strength of exhaust, the absorption stop valve 9a adheres to a cylindrical body 9b arranged above so as to maintain the closed state of the absorption path 20.

The float 5 shown in FIG. 1 and FIG. 2 is placed on the bottom portion 4a of the lying member L, and as shown in FIG. 4, the liquid waste 21 is guided below the float 5 via a flow path comprised of the interstitial portion 27 formed between the cup portion 5b of the float 5 and the annular member 5a and also the interstitial portion 28 formed between the inner wall 26 of the lying member L and the annular member 5a when the liquid waste 21 flows into the lying member L from the upper portion; subsequently, the float 5 stays afloat at liquid-gas interface of the liquid waste 21 since the float 5 is structured to have a specific gravity less than 1.

The liquid waste 21 absorbed into the lying member L from the absorption port 7 comes around to a bottom portion via the interstitial portion 28 formed between the lying member L and the annular member 5a or the interstitial portion 27 formed between the cup portion 5b of the float 5 and the annular member 5a; then the liquid waste 21 permeates through the water permeable sheet 22 spread and stretched at a peripheral rim portion of the cup portion 5b and contacts to the water-absorptive material 6 so that the water-absorptive material 6 would swell to tear the water permeable sheet 22 and dissolve into the liquid waste 21 contained inside the lying member L to solidify the liquid waste 21 into a gel, or otherwise, the liquid waste 21 contacts to the water-soluble film spread and stretched at a peripheral rim portion of the cup portion 5b and dissolves the water-soluble film so that the water-absorptive material 6 dissolve into the liquid waste 21 contained inside the lying member L to solidify the liquid waste 21 into a gel.

Hereinafter an operating procedure and an operation of the liquid waste disposal apparatus 1 shall be described. The lying member L is preserved and transported in a state where the holder 10 remains attached by a method such as sealing the lying member L with a vinyl-wrapping container. In thus situation, the catch 10a arranged at the holder 10 could be laid down to both sides of the lid 3, and the lying member L could be preserved and transported in a relatively compact manner since the lying member L itself is flexible.

At a time for operation, the lying member L is prepared in correspondence with the number of the bottle M arranged in a straight line at the stand 2, and then, the adjustment handle 17a is turned to a prescribed direction shown in FIG. 3 so as to turn the controller 17 off, and then an adapter 18a of the primary absorption hose 18 is connected to a terminal takeout port or an air pump of a medical gas piping installation (not shown).

Next, the canister bottle 12 of the stand 2 is opened to insert the lying member L into all of the bottles M, and then, the connection pipe 15 rotatively attached to the discharge port 8 formed at the lid 3 of the ceiling portion of the respective lying members L is inserted and connected to the absorption port 7 formed at the lid 3 of the ceiling portion of the lying member L adjoined to the left side in FIG. 4.

The end portion on the side of the valve member 14a of the patient hose 14 is inserted and connected to the absorption port 7 formed at the lid 3 of the ceiling portion of the lying member L1 of the primary canister bottle E1 and further, in means for closure, the closing stopper 16 formed at the lid 3 of the lying member L4 is connected to the connection pipe 15 in which the connection pipe 15 is connected to the discharge port 8 formed at the lid 3 of the lying member L4 of the last and fourth canister bottle E4.

Next, the canister head 12 is closed and locked to the stand 2. Before the beginning of absorption, the float 5 is arranged at the bottom portion 4a of the lying member L as shown in FIG. 3 owing to the weight of the float 5 itself.

Then, the adjustment handle 17a of the controller 17 is turned to turn the controller 17 for adjusting to a prescribed absorption pressure. In this case, the negative pressure of the primary absorption hose 18 causes the inside of the lying member L to become negative pressure via the absorption path 13 formed at the respective canister heads 12 and the absorption path 20 of the exhaust port 9 formed at the lid 3 of the ceiling portion of the respective lying members L; further, the gaps between the respective bottles M and the respective lying members L are also caused to become negative pressure via the absorption path 19 in air-communication with the gaps between the respective bottles M and the respective lying members L.

In this process, the presence of absorption pressure inside the lying member L is to be confirmed by closing a tip of the patient hose 14 and whether or not the lying member L inflates along the bottle M is also to be confirmed.

When an absorption of the liquid waste 21 is started after a tip of the patient hose 14 is applied to such as an affected area of the patient, as shown in FIG. 4, the liquid waste 21 from the patient hose 14 is guided into the lying member L via the absorption port 7 formed at the lid 3 of the lying member L1 of the primary canister bottle E1.

The liquid waste 21 absorbed into the lying member L1 reaches below the float 5 via the interstitial portion 28 formed between the lying member L1 and the annular member 5a of the float 5 or via the interstitial portion 27 formed between the cup portion 5b and the annular member 5a of the float 5.

Since the float 5 has a specific gravity less than the float 5, the float maintains a position at the level of the liquid waste 21 and stays afloat at liquid-gas interface; thus, the liquid waste 21 permeates through the water permeable sheet 22 spread and stretched at a bottom surface of a peripheral rim portion of the cup portion 5b of the float 5 and contacts to the water-absorptive material 6 so that the water-absorptive material 6 would swell to tear the water permeable sheet 22 and spread among the liquid waste 21 and solidify the liquid waste 21 into a gel, or otherwise, the water-soluble film spread and stretched at a bottom surface of a peripheral rim portion of the cup portion 5b of the float 5 dissolves so that the water-absorptive material 6 would spread among the liquid waste 21 to solidify the liquid waste 21 into a gel.

Even after the progress of the absorption of the liquid waste 21, the water-absorptive material 6 could effectively spread among the liquid waste 21 absorbed afterwards and solidify thus liquid waste 21 into a gel since the float 5 constantly stays afloat at the liquid-gas interface.

Further, since the float 5 constantly stays afloat at the liquid-gas interface, the amount of the absorbed liquid waste 21 could easily be visually recognized so that the float 5 could function as a level gauge as well. Therefore, it is suitable for such as the annular member 5a or the cup portion 5b of the float 5 to be formed with a material having a color distinguishable with the color of the liquid waste 21 or a distinguishing color such as a florescent color.

As shown in FIG. 4, as the absorption process of the liquid waste 21 progresses, the float 5 elevates to the ceiling portion of the lying member L and then, the ceiling edge surface 5b1 serving as the upward-pushing portion of the cup portion 5b of the float 5 pushes the absorption stop valve 9a upward against the weight of the absorption stop valve 9a so that the absorption path 20 becomes closed and the absorption pressure from the exhaust port 9 would cease, as a manner as primary canister bottle E1 of FIG. 4.

With the cease of the absorption pressure inside the lying member L1, an absorption pressure of the L2 adjoined at the left side of the lying member L1 in FIG. 4 affects the inside of the lying member L1 via the absorption path 13 of the stand 2, the absorption path 20 of the exhaust port 9 of the lying member L2, the absorption port 7 of the lying member L2, the connection pipe 15, the discharge port 8 of the lying member L1; the not-yet gelled liquid waste 21 absorbed above the float 5 inside the lying member L1 is absorbed into the lying member L2 via the discharge port 8 of the lying member L1, the connection pipe 15 and the absorption port of the lying member L2.

In the same manner as the foregoing lying member L1, the float 5 elevates and stays afloat at the level of the liquid waste 21 in correspondence with the rise in the level of the liquid waste 21 contained inside the lying member L2, and when the float 5 reaches the ceiling portion of the lying member L2, the ceiling edge surface 5b1 of the float 5 pushes the absorption stop valve 9a upward to close the absorption path 20 and cease the absorption pressure of the lying member L2.

Likewise, an absorption pressure of the lying member L3 adjoined to the lying member L2 absorbs the absorbed liquid waste 21 contained above the float 5 of the lying member L2 into the lying member L3 via the discharge port 8 of the lying member L2, the connection pipe 15 and the absorption port of the lying member L3.

In the same manner as the foregoing lying members L1, L2, the float 5 elevates and stays afloat at the level of the liquid waste 21 in correspondence with the rise in the level of the liquid waste 21 contained inside the lying member L3, and when the float 5 reaches the ceiling portion of the lying member L2, the ceiling edge surface 5b1 of the float 5 pushes the absorption stop valve 9a upward to close the absorption path 20 and cease the absorption pressure of the lying member L3.

Likewise, an absorption pressure of the lying member L4 adjoined to the lying member L3 absorbs the absorbed liquid waste 21 contained above the float 5 of the lying member L3 into the lying member L4 via the discharge port 8 of the lying member L3, the connection pipe 15 and the absorption port of the lying member L4.

In the same manner as the foregoing lying members L1, L2, L3, the float 5 elevates and stays afloat at the level of the liquid waste 21 in correspondence with the rise in the level of the liquid waste 21 contained inside the lying member L4, and when the float 5 reaches the ceiling portion of the lying member L4, the ceiling edge surface 5b1 of the float 5 pushes the absorption stop valve 9a upward to close the absorption path 20 and cease the absorption pressure of the lying member L4.

Therefore, since the ceiling edge surface 5b1 serving as the upward-pushing portion of the float 5 upwardly pushes and activates the absorption stop valve 9a, the absorption of the liquid waste 21 is automatically ceased before all of the lying members L become full with liquid waste 21; accordingly, the air-pump or the like would not malfunction due to an excessive absorption into the respective lying members L.

After the use of the liquid waste disposal apparatus, the lying member L is taken out from the bottle M by opening the canister head 12 of the stand 2, and then, an end portion of the connection pipe 15 is inserted and connected to the absorption port 7 arranged at the lid 3 wherein another end-portion of the connection pipe is rotatively connected to the discharge port 8 of the lid 3 of the respective lying members L, and then, as shown in FIG. 3, FIG. 5(b) and FIG. 6(a), a cap 24 prearranged to the lid 3 covers the exhaust port 9 arranged at the lid 3 of the respective lying members L for hermetically sealing the lying members L, and subsequently, pulling out the lying member L with the catch 10a of the holder 10 enables easy detachment from the bottle M so that the lying member L could solely be disposed for incineration and the like.

Further, the lying member could be solely stood upright owing to a function of the bottom portion 4a of the lying member L in a state where the liquid waste 21 inside the lying member L is gelled by the water-absorptive material 6.

The liquid waste 21 remaining inside the connection pipe 15 or the patient hose 14 would not drip down during a detachment of the patient hose 14 or the connection pipe 15 from the absorption port 7 owing to a function of the rubber valves 14a1, 15a1 of the valve members 14a, 15a of the connection pipe 15 or the patient hose 14.

Thus structured, the liquid waste 21 absorbed from the upper portion and into the lying member L serving as a container flows under the float 5 via the flow path having the interstitial portion 28 formed between the cup portion 5b of the float 5 and the annular member 5a as well as the interstitial portion 27 formed between inner wall 26 of the lying member L and the annular member 5a.

The annular member 5a serving as the revolution prevention member arranged to the float 5 and restrained by the inner wall 26 of the lying member L serves to prevent the float 5 from revolving in a vertical direction and thus allows the float 5 to steadily stay afloat inside the lying member L. The water-absorptive material 6 serving as the solidifying agent and retained by the cup portion 5b serving as the solidifying agent retaining portion is capable of solidifying the liquid waste 21.

The float 5 itself retains the water-absorptive material 6 so that the water-absorptive material 6 would always be arranged at the liquid-level of the liquid waste 21; subsequently, the liquid waste 21 inside the lying member L could be effectively solidified for enabling the lying member L to be solely and sanitarily disposed.

The activation of the absorption stop valve 9a causes the automatic cease of absorption when the float 5 reaches an upper end portion inside the lying member L owing to a structure where the ceiling edge surface 5b1 serving as the upward-pushing portion is arranged to the float 5 for upwardly pushing and activating the absorption stop valve 9a arranged at the inner-upper portion of the lying member L; the ceiling edge portion 5b1 of the float 5 activates the absorption stop valve 9a to automatically cease the absorption of the liquid waste 21 before the lying members L become full with liquid waste 21; accordingly, the air-pump or the like would not malfunction due to an excessive absorption into the respective lying members L.

Owing to the structure where the cup portion 5b serving as the solidifying agent retaining portion of the float 5 opens facing downward in which the water permeable sheet 22 (e.g. traditional Japanese paper) is spread and stretched at the opening portion, the liquid waste 21 absorbed in from the upper portion of the lying member L flows under the float 5 via the flow path formed of the interstitial portions 27,28 so as to permeate through the water permeable sheet 22 and contact the water-absorptive material 6, and then, the water-absorptive material 6 swells to tear the water permeable sheet 22, and then the water-absorptive material 6 is mixed into the liquid waste 21 from the opening formed at the lower portion of the cup portion 5b for solidifying the liquid waste 21 under the float 5.

Further, owing to the structure where the cup portion 5b serving as the solidifying agent retaining portion of the float 5 opens facing downward in which the water-soluble film is spread and stretched at the opening portion, the liquid waste 21 absorbed in from the upper portion of the lying member L flows under the float 5 via the flow path formed of the interstitial portions 27,28 so as to contact with the water-soluble film and dissolve the water-soluble film, and then, the water-absorptive material 6 is mixed into the liquid waste 21 from the opening formed at the lower portion of the cup portion 5b for solidifying the liquid waste 21 under the float 5.

The liquid waste 5 contained above the float 5 could be guided to the adjoining lying member L in a liquid state without being solidified, and further, the disposal capacity could be easily increased by consecutively connecting numerous lying members L, as shown in FIG. 4.

The float 5 could always remain afloat at the liquid-gas interface by structuring the float 5 to have a specific gravity less than 1; accordingly, the position of a liquid-level could easily be confirmed from outside by confirming the position of the float 5, and further, the amount of the absorbed liquid waste 21 could easily be visually recognized so that the float 5 could also function as a level gauge.

By forming at least one portion of the float 5 into a florescent color or a color distinguishable from the liquid waste 21, the position of the float 5 could easily be visually recognized from outside so that the liquid-surface could easily be recognized and thus, the operator could positively confirm the used state and the remaining capacity of the lying member L.

Although the annular member 5a, the cup portion 5b and the fixing ring 23 of this embodiment is formed from a polypropylene material having a specific gravity less than 1, as long as the specific gravity of the float 5 is less than 1, the material of thus portions is not to be limited to polypropylene.

Although the shape of the float 5 formed as a cup in a face down manner, the shape of the float 5 of this invention is not to be limited and any shape is acceptable as long as the bottom portion of the float 5 is opened (e.g. a cylinder or a polygon having a same top surface as the ceiling-edge surface or a shape having a ring-like float at a center with an arm for retaining the water-absorptive material 6). The inner portion of the cup portion 5b serving as a retaining container for retaining the water-absorptive material 6 is desired to have a ventilation hole, a slit or the like for preventing an accumulation of air.

As examples regarding the retaining means for retaining the water-absorptive material 6 inside the cup portion 5b, the water permeable sheet 22 (e.g. traditional Japanese paper) or the water-soluble film covering the opening portion of the cup portion 5b are described above, however, other means for retaining the water-absorptive material 6 could be used such as a means by solidifying the water-absorptive material 6 with a water-dissolvable filling material, a means by retaining with a water-decomposable non-fabric paper or a non-fabric cloth.

A second, third, fourth and fifth embodiment of the float for a liquid waste disposal apparatus regarding this invention will hereinafter be described with reference to the FIG. 8 through FIG. 11. FIG. 8 through FIG. 11 are perspective views showing the structures of the second, third, fourth and fifth embodiment of the float for a liquid waste disposal apparatus regarding this invention. The symbols of the components having the same structure as the first embodiment shall be indicated using the same symbols.

Figure 8:
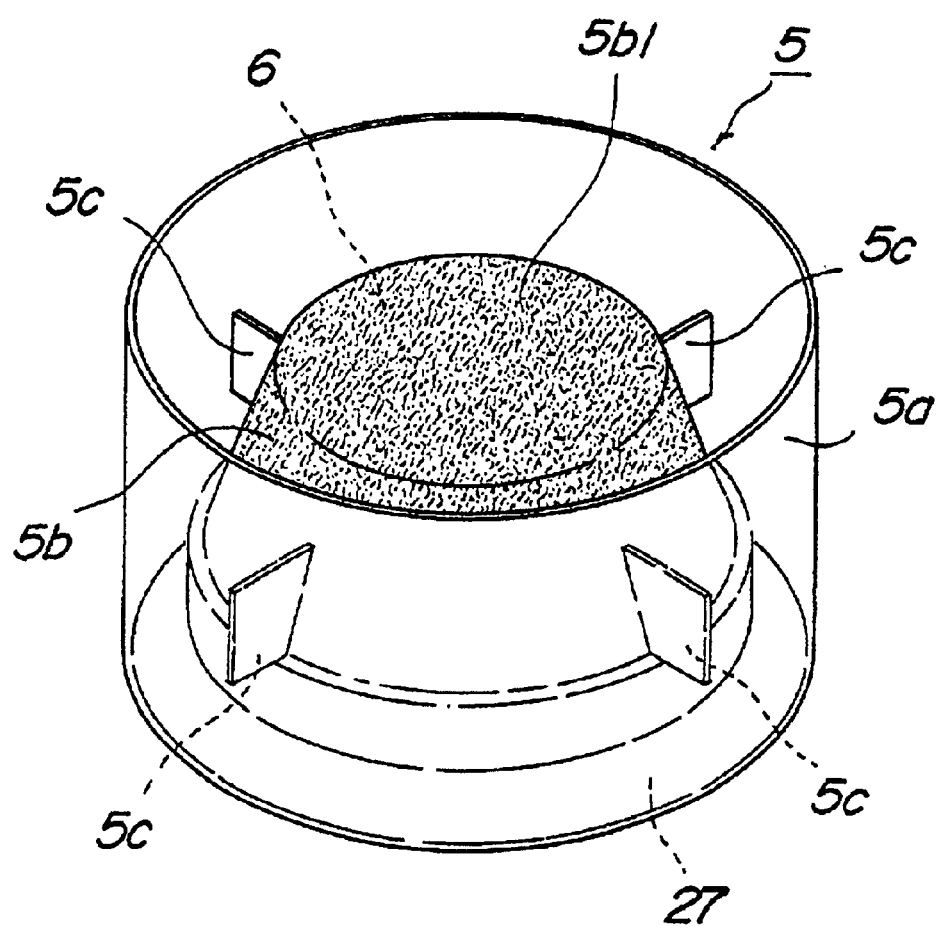
FIG. 8 is a perspective explanatory view showing a structure of a second embodiment of the float for a liquid waste disposal apparatus regarding this invention.

FIG. 8 is a view of the second embodiment showing the annular member 5a serving as a guide member and having a greater length in a height direction (vertical direction in FIG. 1) compared to the first embodiment shown in FIG. 1; and therefore, having a larger region restrained by the inner wall 26 of the lying member L.

Owing to the flexibility of the lying member L, the lying member L could be folded into a smaller size and could expand and contract serving to benefit transportation of the lying member L before being used; however, the float 5 might revolve inside the lying member L during transportation and would require rearranging the position of the revolved float 5 in a vertical direction during a setting of the liquid waste disposal apparatus. With this embodiment, the vertical revolving of the float 5 could be positively prevented by increasing the length of the annular member 5a in a height direction (vertical direction in FIG. 1).

Figure 9:
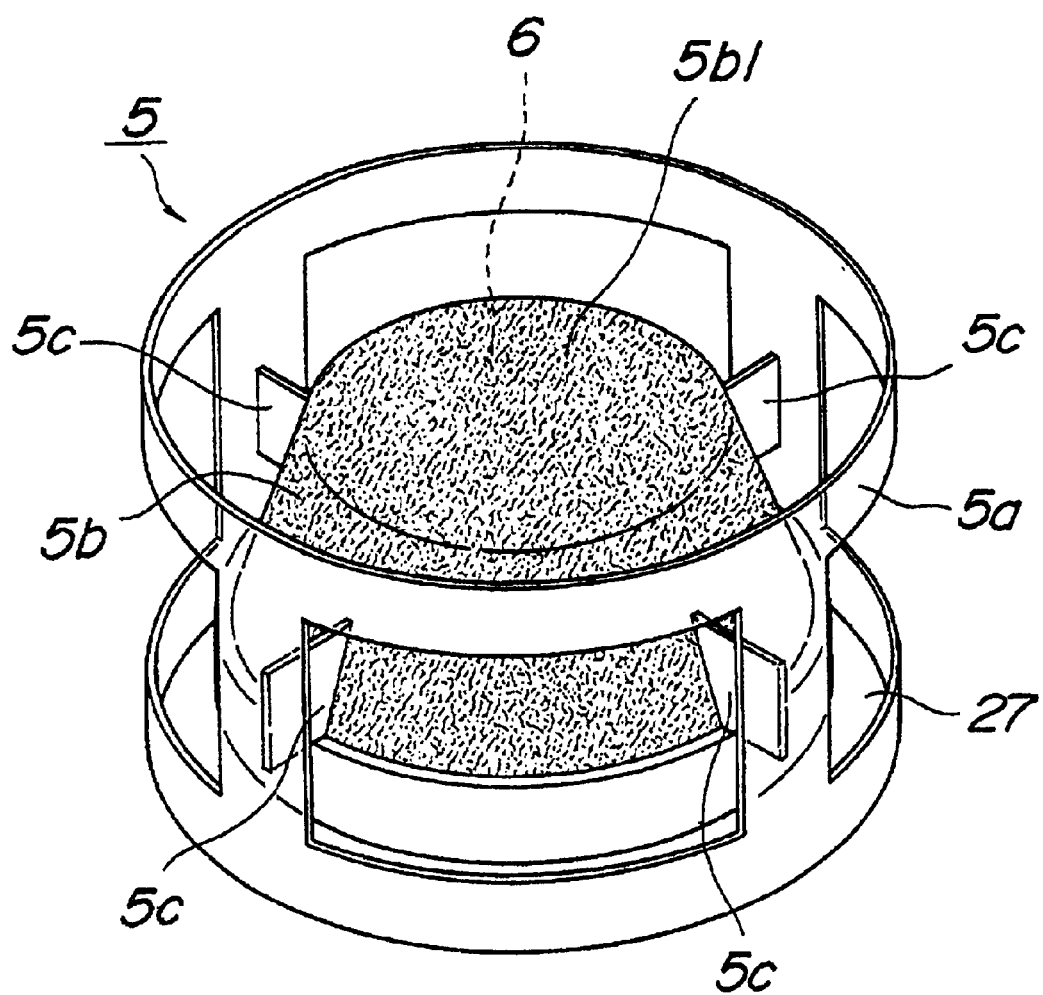
FIG. 9 is a perspective explanatory view showing a structure of a third embodiment of the float for a liquid waste disposal apparatus regarding this invention.

FIG. 9 is a view of the third embodiment showing the annular member 5a serving as a guide member and having a portion structured with an opening. Thus structure enables a reduction in the cost regarding the material of the float 5 and also creates liquid-communication between the interstitial portion 27 formed between the cup portion 5b and the annular member 5a and the interstitial portion 28 formed between the inner wall 26 of the lying member L and the annular member 28 for accelerating a downward flow of the liquid waste 21.

Figure 10:
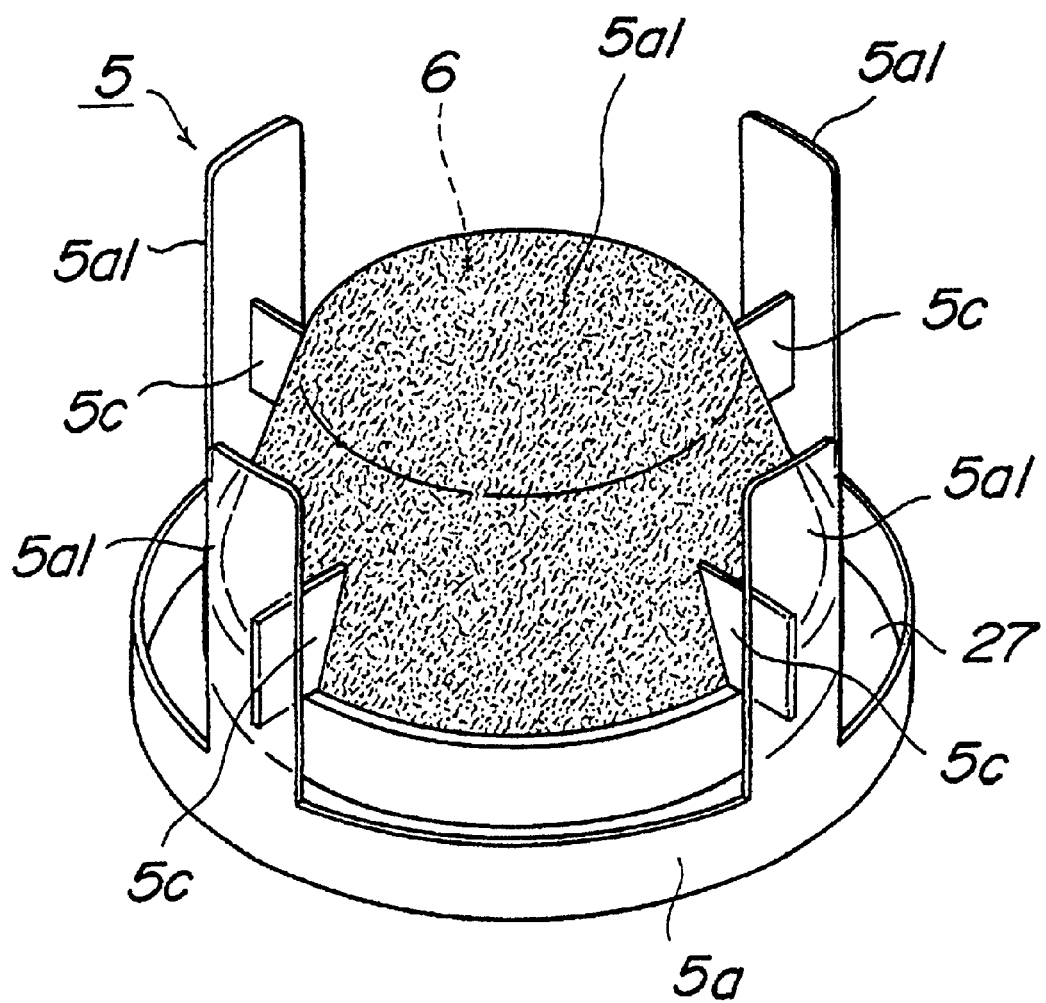
FIG. 10 is a perspective explanatory view showing a structure of a fourth embodiment of the float for a liquid waste disposal apparatus regarding this invention.
Figure 11:
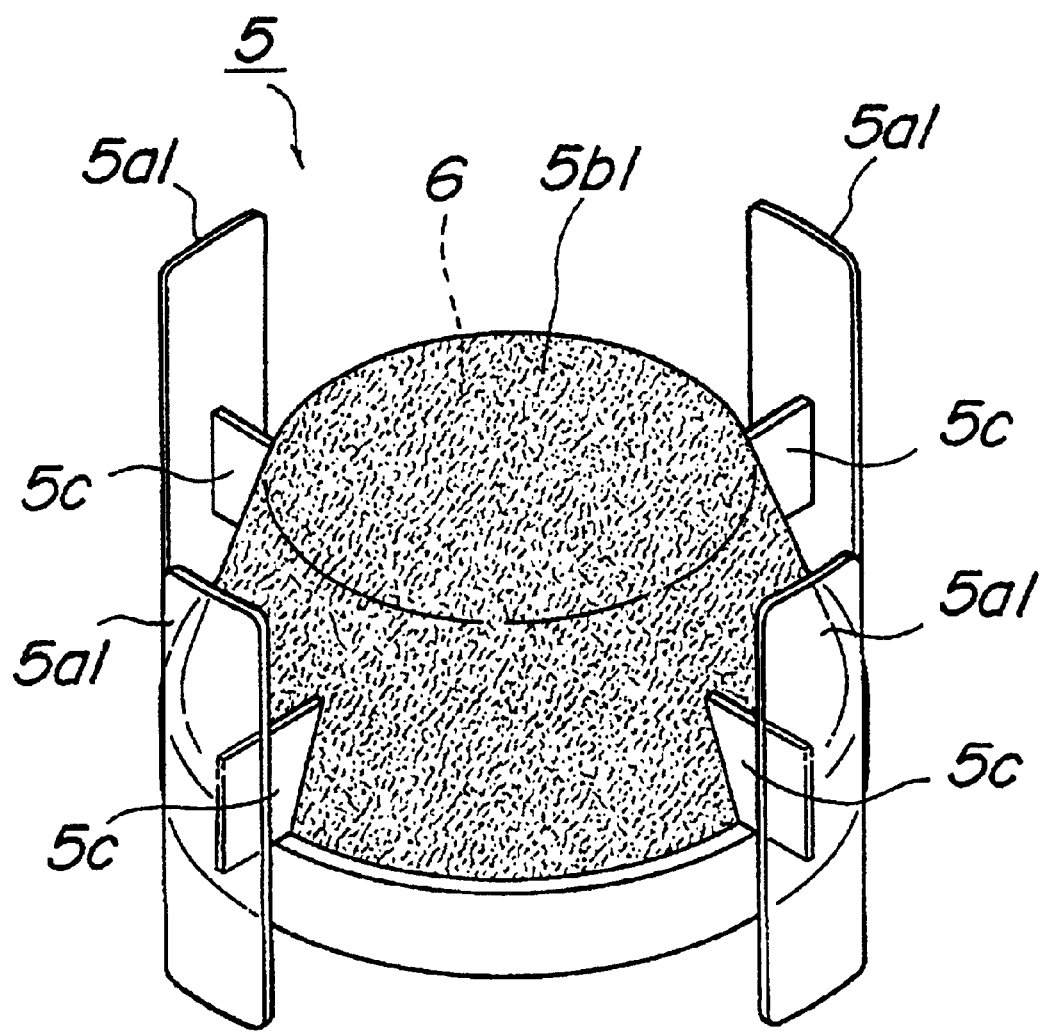
FIG. 11 is a perspective explanatory view showing a structure of a fifth embodiment of the float for a liquid waste disposal apparatus regarding this invention.

FIG. 10 is a view of the fourth embodiment showing the annular member 5a of the third embodiment of FIG. 9 with an upper portion in an omitted state. FIG. 11 is a view of the fifth embodiment showing the annular member 5a of the fourth embodiment of FIG. 10 with a lower portion also in an omitted state while having a plurality of guide members 5a1 supported by the connecting plates 5c.

According to the fourth and fifth embodiment, the guide members 5A1 serving as the revolving prevention portion is restrained by the inner wall 26 of the lying member L for preventing the float 5 from revolving in a vertical direction. Thus structured, the cost for the material of the float 5 would further reduce and the downward flow of the liquid waste 21 would further be accelerated.

The other structural portions regarding the second, third, fourth, and fifth embodiments have the same structure and effect as that of the first embodiment.

Figure 12:
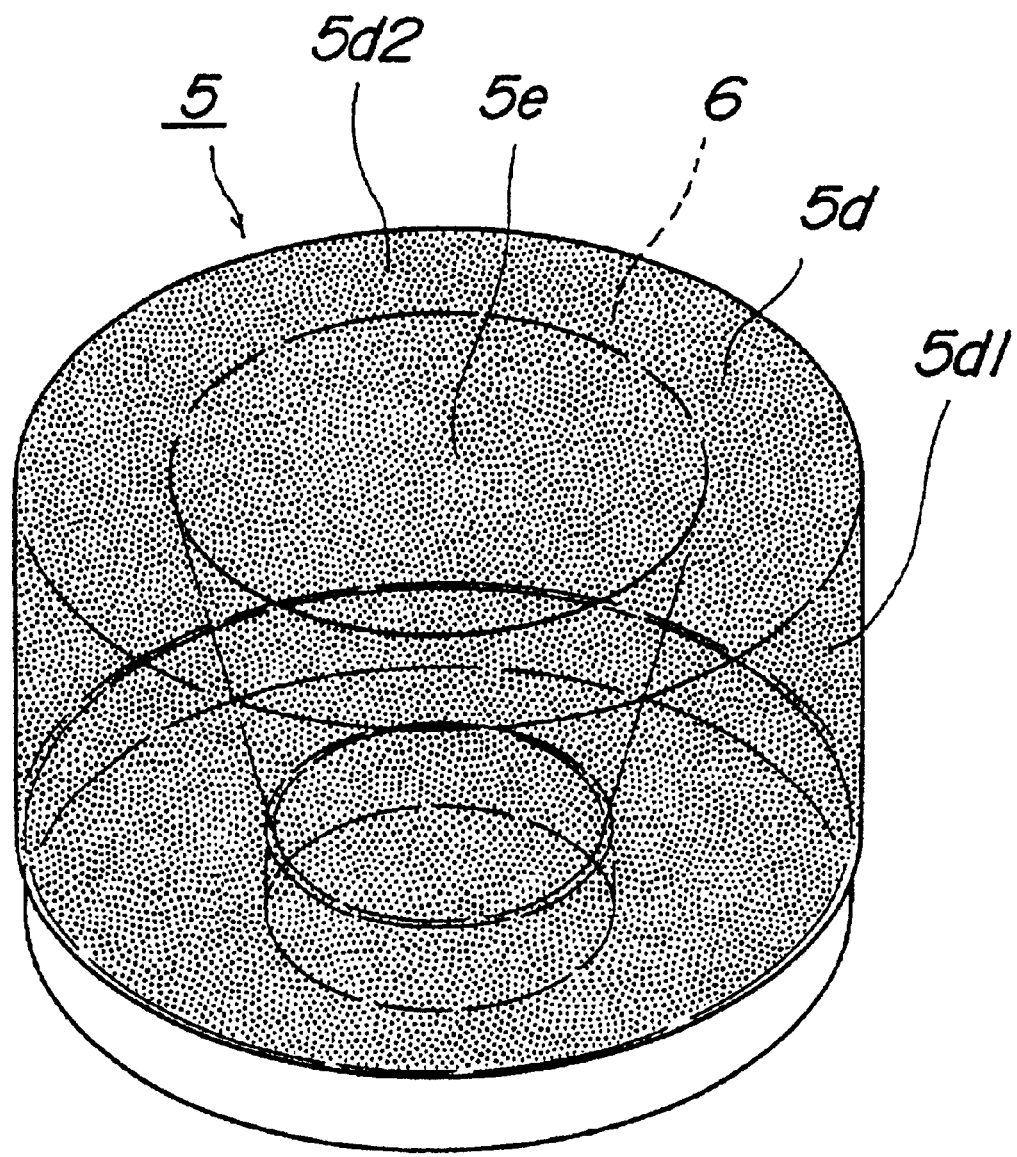
FIG. 12 is a perspective explanatory view showing a structure of a sixth embodiment of the float for a liquid waste disposal apparatus regarding this invention.
Figure 13:
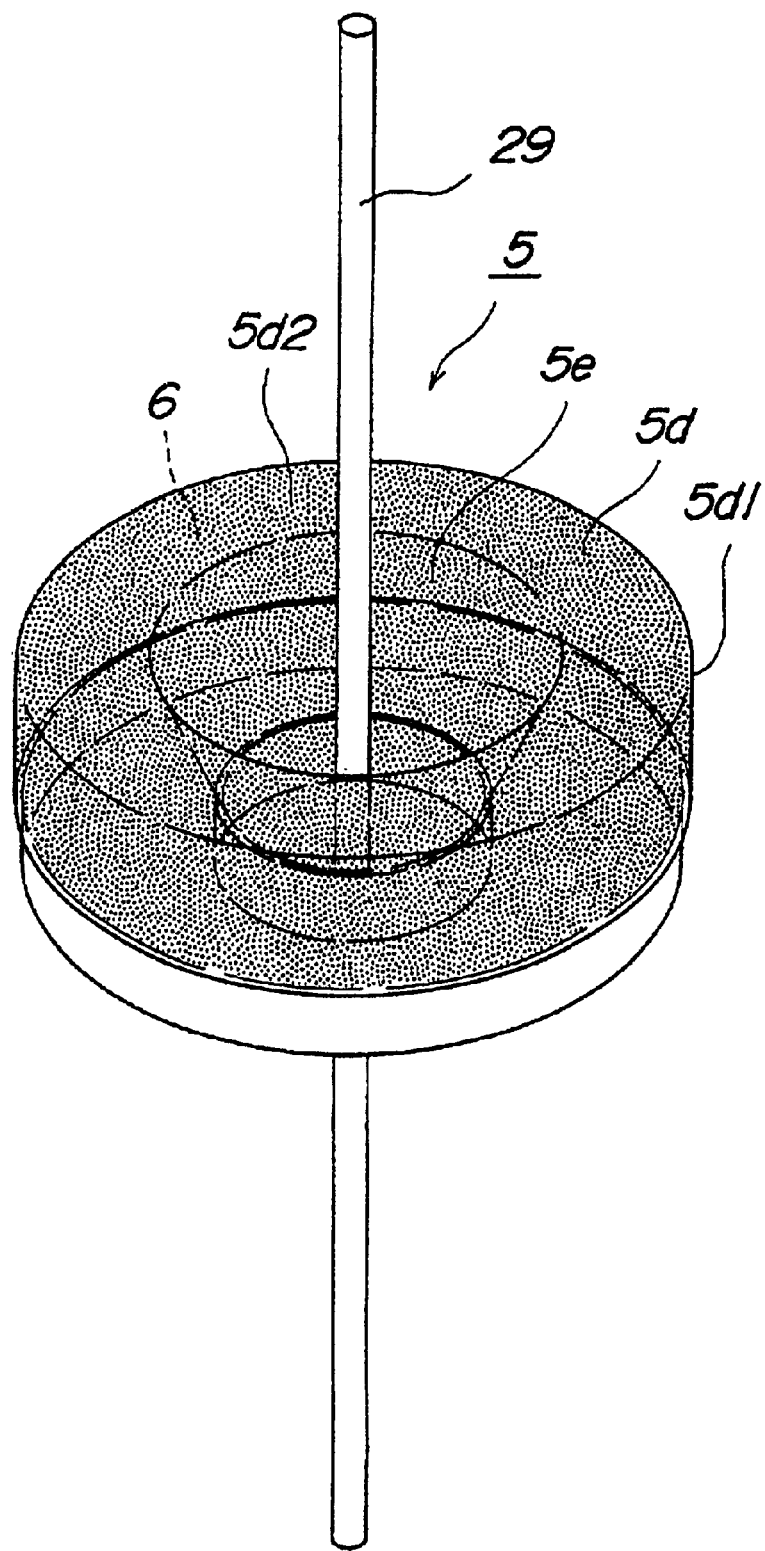
FIG. 13 is a perspective explanatory view showing a structure of a seventh embodiment of the float for a liquid waste disposal apparatus regarding this invention.

A sixth and seventh embodiment of the float for a liquid waste disposal apparatus regarding this invention will hereinafter be described with reference to the FIG. 12 and FIG. 13. FIG. 12 is a perspective explanatory view showing the structure of the sixth embodiment and FIG. 13 is a perspective explanatory view showing the structure of the seventh embodiment. The symbols of the components having the same structure as the foregoing embodiments shall be indicated using the same symbols.

FIG. 12 is a view of the sixth embodiment showing the float body 5 formed of an annular solidifying agent retaining portion 5d for retaining the absorption stop valve 6 serving as the solidifying agent, wherein the hollow portion 5e of the annular solidifying agent retaining portion 5d and the interstitial portion formed between the sidewall 5d1 of the solidifying agent retaining portion 5d and the inner wall 26 of the lying member L forms a flow path for flowing downward the liquid waste 21 absorbed from the upper portion of the lying member L.

The sidewall 5d1 of the annular solidifying agent retaining portion 5d is restrained by the inner wall 26 of the lying member L for preventing the float 5 from revolving in a vertical direction. The sidewall 5d1 of the solidifying agent retaining portion 5d serving as a revolution prevention portion enables a simple structure.

According to this embodiment, the absorption stop valve 9a is disposed at the lid 3 of the lying member L and arranged at a position facing the ceiling edge surface 5d2 of the annular solidifying agent retaining portion 5d serving as the upward-pressing portion, and when the float 5 reaches the upper edge portion of the lying member L, the ceiling edge surface 5d2 of the float 5 activates the absorption stop valve 9a so as to automatically cease absorption for automatically stopping the liquid waste 21 from being absorbed before the lying member L becomes full with liquid waste 21.

FIG. 13 is a view of the seventh embodiment structured with a stick-like, or a pipe-like, or a wire-like revolution prevention member 29 inserted through the hollow portion 5e for preventing the float 5 from revolving in a vertical direction.

The revolution prevention member 29 is structured having a length in correspondence with a height of the lying member L, wherein the revolution prevention member 29 could be fixed to both or either one of the bottom portion 4a and the lid 3 of the lying member L or, the revolution prevention member 29 could be contained inside the lying member L in a manner fixed to neither of the above. Same as the lying member L, the revolution prevention member 29 is desired to have a flexible structure for the convenience of storage and transportation.

Structuring the revolution prevention member 29 positively prevents the float 5 from vertically revolving even when the height of the float 5 is substantially short. The other structural portions are comparatively the same as that of the sixth embodiment.

The other structural portions regarding the sixth and seventh embodiments have the same structure and effect as that of the foregoing embodiment.

Although the foregoing embodiments are examples describing a float 5 contained inside the flexible lying member L, the float could be contained inside a container without a flexible structure.

This invention having the aforementioned structure and effect enables the content inside a container to be easily visually recognizable and allows a faster and steadier solidification of an absorbed liquid waste.

According to the float for a liquid waste disposal apparatus claim 1, the liquid waste absorbed from above and into the container via the flow path flows under the float. The revolution prevention member arranged to the float and restrained by the inner wall of the container serves to prevent the float from revolving in a vertical direction and allows the float to steadily float inside the container. The solidifying agent retained by the solidifying agent retaining portion solidifies the liquid waste.

The container could be structured having the solidifying agent at the inner side since the float itself retains the solidifying agent; subsequently, the liquid waste could be solidified inside the container to enable the container to be solely and sanitarily disposed.

Forming the revolution prevention member by arranging the guide members at the sidewall of the float body or the outer peripheral portion of the float body enables a simple and desirable structure.

Forming the flow path by arranging the interstitial portion formed between the sidewall of the float body and the inner wall of the container and/or the interstitial portion formed between the float body and the outer peripheral portion of the float body enables a simple and desirable structure.

According to the float for a liquid waste disposal apparatus claim 4, the liquid waste absorbed from above and into the container via the flow path formed of the annular solidifying agent retaining portion flows under to the float. The annular solidifying agent retaining portion restrained by the inner wall of the container serves to prevent the float from revolving in a vertical direction and allows the float to steadily float inside the container. The solidifying agent retained by the annular solidifying agent retaining portion solidifies the liquid waste.

The container could be structured having the solidifying agent at the inner side since the float itself retains the solidifying agent; subsequently, the liquid waste could be solidified inside the container to enable the container to be solely and sanitarily disposed.

According to the float for a liquid waste disposal apparatus claim 5, the liquid waste absorbed from above and into the container via the flow path formed of the annular solidifying agent retaining portion flows under to the float. A stick-like, or pipe-like, or wire-like revolution prevention member is inserted through the hollow portion of the annular solidifying agent retaining portion for preventing the float from revolving in a vertical direction and for allowing the float to steadily float inside the container. The solidifying agent retained by the annular solidifying agent retaining portion solidifies the liquid waste.

The container could be structured having the solidifying agent at the inner side since the float itself retains the solidifying agent; subsequently, the liquid waste could be solidified inside the container to enable the container to be solely and sanitarily disposed.

The activation of the absorption stop valve causes the automatic cease of absorption when the float reaches an upper end portion inside the container owing to the structure where the ceiling edge surface serving as the upward-pushing portion is arranged to the float for upwardly pushing and activating the absorption stop valve arranged at the inner-upper portion of the container; the ceiling edge portion of the float activates the absorption stop valve to automatically cease the absorption of the liquid waste before the container becomes full with liquid waste; accordingly, the air-pump or the like would not malfunction due to an excessive absorption into the container.

The solidifying agent retaining portion is open in a downward direction having the water permeable sheet (e.g. traditional Japanese paper) spread and stretched at the opening portion, and then, the liquid waste absorbed in from the upper portion of the container flows under the float via the flow path so as to permeate through the water permeable sheet and contact the water-absorptive material, and then, the water-absorptive material swells to tear the water permeable sheet, and then the water-absorptive material is mixed into the liquid waste from the opening formed at the lower portion of the cup portion for solidifying the liquid waste under the float.

The float could always remain afloat at the liquid-gas interface by structuring the float to have a specific gravity less than 1; accordingly, the position of a liquid-level could easily be confirmed from outside by confirming the position of the float, and further, the amount of the absorbed liquid waste could easily be visually recognized so that the float could also function as a level gauge.

By forming at least one portion of the float into a florescent color or a color distinguishable from the liquid waste, the position of the float could easily be visually recognized from outside so that the liquid-surface could easily be recognized and thus, the operator could positively confirm the used state and the remaining capacity of the container.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

What is claimed is:

1. A float for a liquid waste disposal apparatus contained in a floatable state inside a container for containing an absorbed liquid waste comprising:
   a solidifying agent retaining portion for retaining a solidifying agent;
   a revolution prevention member having a guide member arranged at a sidewall of a float body or at an outer peripheral portion of the float body, said revolution prevention member being restrained by an inner wall of the container to prevent revolution in a vertical direction; and
   a flow path for flowing downward the liquid waste absorbed from an upper portion into the container.

2. The float for a liquid waste disposal apparatus according to claim 1, wherein the flow path is structured having an interstitial portion formed between the sidewall of the float body and the inner wall of the container and/or an interstitial portion formed between the float body and the guide member arranged at the outer peripheral portion of the float body.

3. The float for a liquid waste disposal apparatus according to claim 1, wherein an absorption stop valve is arranged at an inner side of an upper portion of the container in which the absorption stop valve is activated when pushed upwards by an upward-pushing portion.

4. The float for a liquid waste disposal apparatus according to claim 1, wherein the solidifying agent retaining portion is open downward and has a water permeable sheet or a water-soluble film spread and stretched at thus opening portion.

5. The float for a liquid waste disposal apparatus according to claim 1, wherein the float is structured so that a specific gravity would be less than 1.

6. The float for a liquid waste disposal apparatus according to claim 1 in which at least one portion is of a florescent color or is of a color distinguishable between a color of the liquid waste.

7. The float for a liquid waste disposal apparatus according to claim 2, wherein an absorption stop valve is arranged at an inner side of an upper portion of the container in which the absorption stop valve is activated when pushed upwards by an upward-pushing portion.

8. The float for a liquid waste disposal apparatus according to claim 2, wherein the solidifying agent retaining portion is open downward and has a water permeable sheet or a water-soluble film spread and stretched at thus opening portion.

9. The float for a liquid waste disposal apparatus according to claim 3, wherein the solidifying agent retaining portion is open downward and has a water permeable sheet or a water-soluble film spread and stretched at thus opening portion.

10. The float for a liquid waste disposal apparatus according to claim 2, wherein the float is structured so that a specific gravity would be less than 1.

11. The float for a liquid waste disposal apparatus according to claim 3, wherein the float is structured so that a specific gravity would be less than 1.

12. The float for a liquid waste disposal apparatus according to claim 4, wherein the float is structured so that a specific gravity would be less than 1.

13. The float for a liquid waste disposal apparatus according to claim 2, in which at least one portion is of a florescent color or is of a color distinguishable between a color of the liquid waste.

14. The float for a liquid waste disposal apparatus according to claim 3, in which at least one portion is of a florescent color or is of a color distinguishable between a color of the liquid waste.

15. The float for a liquid waste disposal apparatus according to claim 4, in which at least one portion is of a florescent color or is of a color distinguishable between a color of the liquid waste.

16. The float for a liquid waste disposal apparatus according to claim 5, in which at least one portion is of a florescent color or is of a color distinguishable between a color of the liquid waste.

* * * * *